United States Patent
Sabol et al.

(10) Patent No.: US 7,492,931 B2
(45) Date of Patent: Feb. 17, 2009

(54) IMAGE TEMPORAL CHANGE DETECTION AND DISPLAY METHOD AND APPARATUS

(75) Inventors: John M. Sabol, Sussex, WI (US); Maggie Mei-Kei Fung, Waukesha, WI (US); Vianney Pierre Battle, Milwaukee, WI (US); Gopal B. Avinash, New Berlin, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 820 days.

(21) Appl. No.: 10/723,861

(22) Filed: Nov. 26, 2003

(65) Prior Publication Data

US 2005/0113961 A1    May 26, 2005

(51) Int. Cl.
*G06K 9/00*    (2006.01)
*G06F 19/00*    (2006.01)

(52) U.S. Cl. ...................... 382/128; 700/182
(58) Field of Classification Search ................. 382/128, 382/129, 130, 131, 132, 133, 134; 600/407, 600/425, 300, 410, 463; 128/906, 920; 378/4, 378/8, 21, 23–27, 92, 98.6, 98.11, 98.12, 378/101, 901

See application file for complete search history.

(56) References Cited

U.S. PATENT DOCUMENTS

| | | | | |
|---|---|---|---|---|
| 5,359,513 A | * | 10/1994 | Kano et al. | 382/128 |
| 5,361,763 A | * | 11/1994 | Kao et al. | 600/410 |
| 5,598,481 A | * | 1/1997 | Nishikawa et al. | 382/130 |
| 5,807,256 A | * | 9/1998 | Taguchi et al. | 600/425 |
| 6,075,879 A | * | 6/2000 | Roehrig et al. | 382/132 |
| 6,421,454 B1 | * | 7/2002 | Burke et al. | 382/131 |
| 6,836,558 B2 | * | 12/2004 | Doi et al. | 382/131 |
| 6,909,792 B1 | * | 6/2005 | Carrott et al. | 382/128 |
| 7,054,473 B1 | * | 5/2006 | Roehrig et al. | 382/128 |
| 2001/0007593 A1 | | 7/2001 | Oosawa | |

OTHER PUBLICATIONS

Pennec, et al., Non-rigid MR/US Registration for Tracking Brain Deformations, Sophia Antipolis Cedex, France.

* cited by examiner

*Primary Examiner*—Abolfazl Tabatabai
(74) *Attorney, Agent, or Firm*—Fletcher Yoder

(57) ABSTRACT

A technique is provided for analysis of image datasets acquired at different points in time. Computer aided algorithms are implemented for identification and classification of features of interest, and for comparison of such features which have evolved over time as represented by the image data. The algorithms may be specifically adapted to analyze temporal change images. Such algorithms may also be used to efficiently launch temporal change analysis only when particular features of interest are possibly present in the image data.

20 Claims, 6 Drawing Sheets

IMAGE TEMPORAL CHANGE DETECTION AND DISPLAY METHOD AND APPARATUS

BACKGROUND OF THE INVENTION

The present invention relates generally to a field of imaging systems. In particular, the invention relates to a technique for analyzing image data to recognize features of interest and comparing resulting analyses with similar analyses performed on image data collected at different points in time in computationally and workflow-efficient manners.

Many applications exist for digital imagery. Such applications range from medical diagnostic imaging to part detection and analysis, parcel screening, and so forth. Similarly, many different types of imaging systems are currently available, some of which span certain of these applications. Imaging systems range from traditional photographic systems to much more complex magnetic resonance imagine (MRI) system, computed tomography (CT) systems, positron emission tomography (PET) systems, ultrasound systems, X-ray systems, and so forth. In each of these systems, some type of image data acquisition circuitry detects input data which is used to codify individual picture elements or pixels in a matrix. When reconstructed, the pixels can be viewed in a composite image which is useful to the viewer for various intended purposes.

Regardless of the origin of pixilated image data, many new uses are being explored which enhance the usefulness of the data for various purposes. For example, in medical imaging, as well as in other fields, such as parcel inspection, image data is analyzed to recognize structures encoded in the pixels, that may be representative of features of particular interest. In the medical field these may include specific anatomies, anomalies, pathologies, and so forth. In automated computer aided or computer assisted processes, computers can now identify certain such features which can be highlighted to a user to augment or aid in diagnosis and treatment of disease, or to analyze various states of wellness. Similarly, in other contexts, such automated recognition and classification processes can greatly assist human viewers and readers by pointing out potential objects of concern or interest.

In many contexts, particularly in medical imaging, images are created of the same subject or anatomy at different points in time. Certain of these images may depict anatomies or anomalies, such as growths, lesions, or other conditions which change over time. The detection of change in medical images of a patient acquire two different instances in time would be of great potential for improving diagnosis and treatment of disease, and for monitoring response to such treatment. More generally, however, such change can be useful in tracking development and growth, or for providing an indication of any meaningful change overtime, both within and outside the medical context. Certain, "temporal subtraction" applications have been proposed. In certain such applications dissimilarity between images is calculated using a simple pixel-by-pixel subtraction approach of registered images. However, simple subtraction results in images of poor contrast. Moreover, such approaches are not sufficiently robust when two initial images are acquired using different techniques or modalities. Moreover, such approaches do not incorporate an indication of a confidence level in the magnitude of the dissimilarity measurement.

In a temporal change image, resulting pixel values, which may be displayed as gray levels in a monochrome image, or proportional to the difference or dissimilarity in pixel values between two input images acquired with temporal separation. The input images may require registration and may be processed to compensate for several factors, such as the difference in positioning of the subject during two image acquisition sessions, differences in acquisition parameters, differences in bit resolution of the images, and differences in any pre- or post-processing that may have been applied to images. Any errors in registration of the two images may result in significantly large values in the dissimilarity image due to the presumption that much more significant changes have occurred in the images or between the images due to the misalignment. For example, if the resulting registration is not perfect, the temporal analysis image of the subject resulting from two identical images will not be a zero-value image as would be anticipated given the identity of the images. That is, for identical images, the process should result in no contrast whatsoever in the dissimilarity image. These non-zero elements of the dissimilarity image represent artifacts that could be mistaken for temporal change in the subject. Such artifacts and the lack of standard anatomical features renders radiographic interpretation of temporal subtracted images challenging for a radiologist or other user, especially when given the unfamiliarity of such users with the appearance of such images. In general, a dissimilarity image summarizes only differences between two compared images. Thus, unlike conventional images that reproduce aspects of a subject in an intuitive manner, this similarity images will generally only illustrate changes in the subject as dark or light regions, lines, and so forth. The images can, of course, be superimposed or otherwise associated with the original images, although developments in the field have not risen to a level as yet to satisfactory in this regard.

The advent and proliferation of digital imaging has enabled rapid electronic access to a variety of information, particularly patient information in the medical field, and the ability to perform rapid advanced image processing and analysis. For example, integration of digital acquisition coupled to a data repository in a hospital or other network enables rapid calculation and display of temporal change images. In addition, these technologies have enabled the practical use of computer aided detection and diagnosis (CAD) techniques and radiology. Such techniques generally serve to identify and classify various features of interest reproduced or detectable within the image data. Such "machine vision" tools have been developed to improve sensitivity, specificity and efficiency of radiologists in the interpretation of images.

Little or nothing has been done in the field, however, as yet for enhancing the utility of temporal change images, that is, images compared to one another and analyzed to detect evolution of features or other changes within the images. There is a need, at present, for further enhancement in the existing techniques, and creation of new techniques for performing complex analyses of images taken at different points in time so as to provide a useful indication of changes occurring in an image subject.

BRIEF DESCRIPTION OF THE INVENTION

The present invention provides a novel technique for analysis of images created at different points in time designed to respond to such needs. The technique may be used for images from any suitable modality or imaging system, including complex imaging systems used in medical part and parcel inspection, but also conventional photographic systems. The present technique provides for accessing image data representative of a subject created at different points in time, the points in time being separated by any useful span, from fractions of a second to months or even years. The technique also greatly facilitates the workflow and efficiency in carrying out the process of comparison and analysis. In particular, CAD techniques may be applied both for the original screening of image data for analysis, as well as to launch such screening where appropriate.

DETAILED DESCRIPTION OF SPECIFIC EMBODIMENTS

Figure 1:
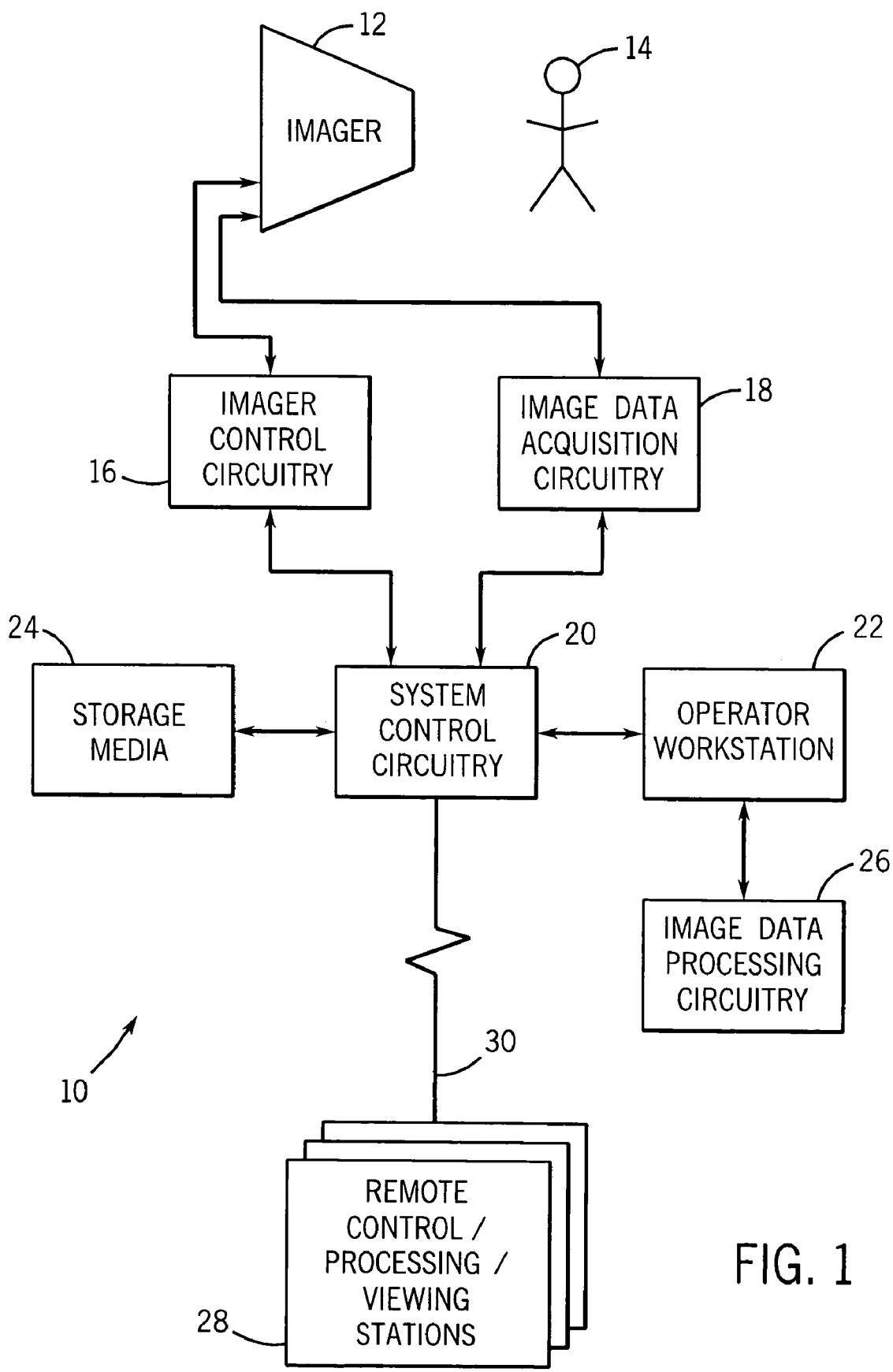
FIG. 1 is a diagrammatical representation of an exemplary imaging system used to create image data at different points in time for analysis in accordance with the present techniques.

Turning now to the drawings and referring first to FIG. 1, an imaging system 10 is illustrated generally as including an imager 12 for creating image data of a subject 14. Although a human figure is generally shown as the subject 14, it should be borne in mind that any appropriate subject could be imaged. In the present context, for example, the subject may be human or animal, animate or in-animate, such as manufactured parts, naturally occurring subjects and so forth. Indeed, the imaging system 10 may be any suitable type of system that produces digitized image data based upon some imaging physics. In the medical imaging context, as elsewhere, such imaging systems may include MRI systems, PET systems, CT system, tomosythesis systems, X-ray systems, ultrasound systems, among many other imaging modalities. The systems may also include conventional photographic imaging systems, that produce digitized image data based upon received radiation of any suitable bandwidth or frequency.

In the diagrammatical view of FIG. 1, the imaging system includes an imager 12 coupled to imager control circuitry 16 and image data acquisition circuitry 18. Depending upon the modality and physics of the system, the imager will typically either emit some type of radiation, as with X-ray, CT, tomosynthesis, and other systems. Other active imaging systems, such as MRI systems, influence subjects by excitation, such as through generation of radio frequency pulses in the presence of controlled magnetic fields. In all these cases, however, the imager is regulated in its operation by the imager control circuitry 16. Such control circuitry may take any suitable form, and typically includes circuitry for activating the imager, receiving radiation or other signals, creating any excitation signals or radiation required for imaging, and so forth. The image acquisition circuitry 18, then, receives and initially processes data received by imager 12. Such initial processing may include conversion of analog signals to digital signals, filtering of the analog or digital signals, scaling or dynamic range adjustments, and the like.

The imager control circuitry 16 and the image data acquisition circuitry 18 are generally regulated by some type of system control circuitry 20. Again, depending upon the nature of the imaging system and the physics involved, the system control circuitry may initiate imaging sequences by exchanging appropriate signals with the imager control circuitry 16. The system control circuitry 20 may also receive the raw or pre-processed image data from the image data acquisition circuitry 18. The system control circuitry 20 may, particularly in more complex systems, be coupled to an operator workstation 22 where an operator selects, configures, and launches examination or imaging sequences. The image data, either raw, partially processed or fully processed, is typically stored in some type of storage media as represented at reference numeral 24. In the present context, such storage media may be part of the system control circuitry 20, the operator workstation 22, or any other component of the overall system. In a medical diagnostics context, for example, such storage media may include local and remote memory, both magnetic and optical, and may include complex picture archive and communication systems (PACS) designed to store and serve image data upon demand.

In the illustration of FIG. 1, the operation workstation 22 is shown as coupled to image data processing circuitry 26. Again, such processing circuitry may actually be distributed throughout the system, and may embody hardware, firmware, and software designed to process the image data to produce reconstructed images for viewing. In accordance with the present techniques described below, the image processing circuitry 26 performs one or more computer aided diagnosis (CAD) routines on the image data to analyze the data with respect to other image data collected at a different point in time. The image data processing circuitry 26 may be local to the imaging system, as illustrated generally in FIG. 1, or may be completely remote from the system, and simply access the image data, as from the storage media 24 for post-processing. Finally, FIG. 1 illustrates various remote control/processing/viewing stations 28 that can be coupled to the imaging system by appropriate network links 30. Such stations may be used for further viewing, analyzing, and processing the image data as described herein.

The imaging system 10, and indeed other imaging systems of the same or different modalities, is used to create images of a subject at various points in time. In accordance with the present technique, these images may be accessed, analyzed and compared to determine whether certain particular features are likely present in the image and therefore in the subject. Moreover, temporal change analysis in accordance with the present techniques permits identification of trends in the development of particular features of interest. In the medical diagnostics context, for example, such temporal change analysis can be used to detect the appearance, growth or reduction of certain anatomical features, disease states, naturally occurring or foreign bodies and objects, and so forth.

Figure 2:
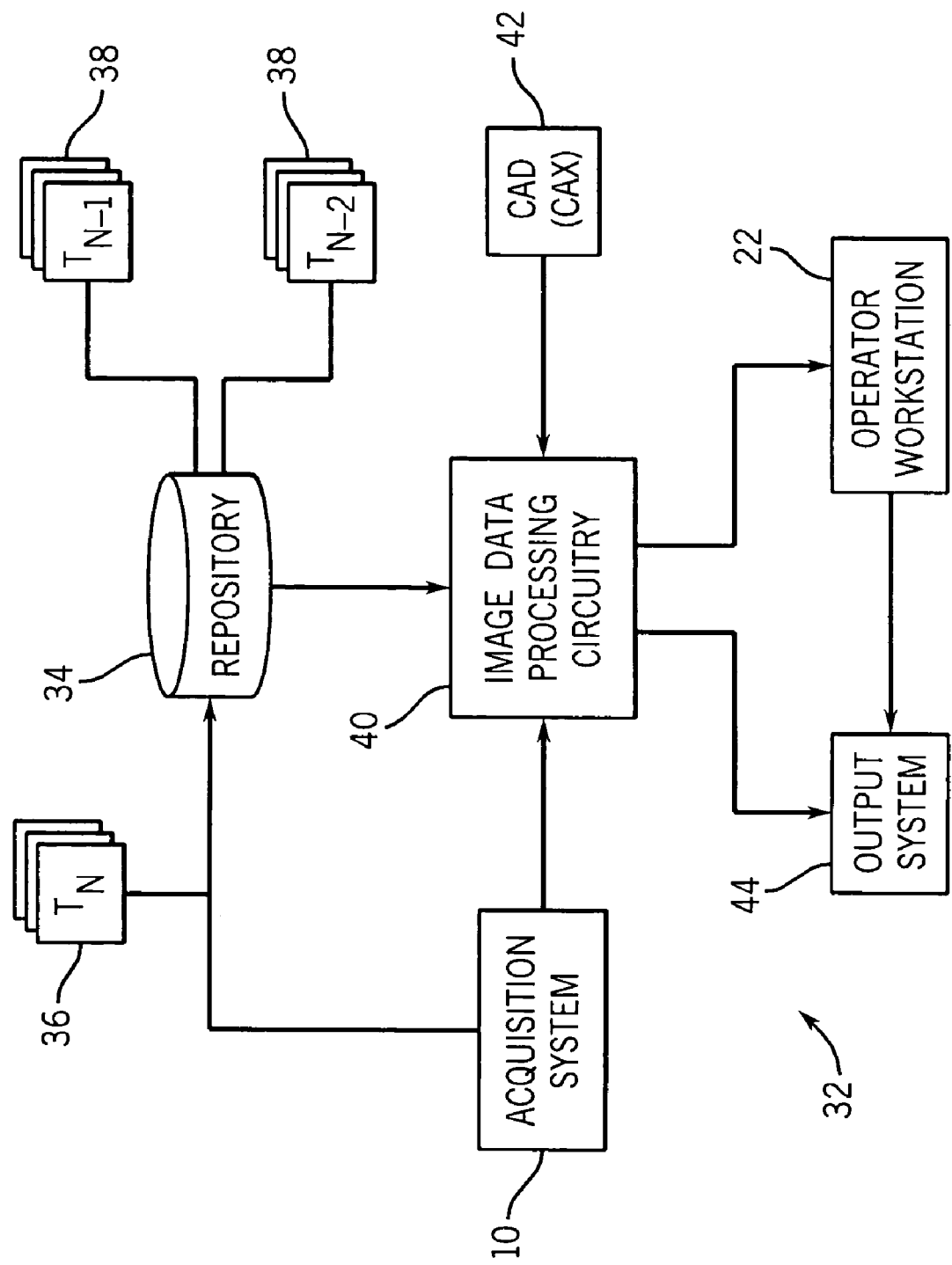
FIG. 2 is a diagrammatical representation of an image processing system for implementing the temporal analysis procedures of the present techniques.

FIG. 2 illustrates diagrammatically a temporal change analysis system designated generally by reference numeral 32. The system incorporates an acquisition system 10 which may be of any suitable type or modality as described above with reference to FIG. 1. The system further includes one or more repositories 34 designed to receive and store image data.

The repository may include any suitable type of memory, typically magnetic media, optical media, and so forth. Moreover, the repository may, in practice, be comprised of a single or many different inter-related storage devices, including devices interconnected via a network. The acquisition system 10 produces images or image sequences at different points in time, such as an image set 36 illustrated in FIG. 2. The repository serves to store such image data, as well as image datasets produced at earlier points in time, as indicated at reference numeral 38 in FIG. 2. As discussed in greater detail below, these various temporally separated image sets may be accessed and analyzed to identify differences or changes between them.

System 32 further includes image data processing circuitry 40. In general, the image data processing circuitry 40 will include various hardware, firmware and software designed to carryout the functions described herein. The processing circuitry may be designed around a general purpose computer or an application-specific computer. Moreover, the image data processing circuitry may, in practice, be a part of the acquisition system 10, or may be completely separate from the acquisition system. Indeed, the image data processing circuitry 40 may perform its operations in near real time as images are acquired by the acquisition system 10, or may perform operations solely in post-processing, by accessing image sets 36 and 38 from the repository 34.

Circuitry 40 draws upon one or more computer aided detection (CAD) or computer aided diagnosis algorithms as represented generally at reference numeral 42 in FIG. 2. As will be appreciated by those skilled in the art, and as described in greater detail below, the CAD algorithm 42 will analyze image data to recognize structures, edges, regions, and other meaningful relationships between the pixilated image data to segment and classify features potentially of interest in the image data. As noted in FIG. 2, in certain instances, the CAD algorithm may be of a much more general nature, generally referred to herein as "CAX". Such algorithms may perform operations other than or in addition to the detection and diagnosis of features of interest. By way of example, such algorithms may serve to initiate acquisition, initiate certain processing, initiate or carryout scheduling, recommended actions, processing strings, and so forth. Where used herein, the term "CAD" should be understood to include any such additional operations.

Figure 3:
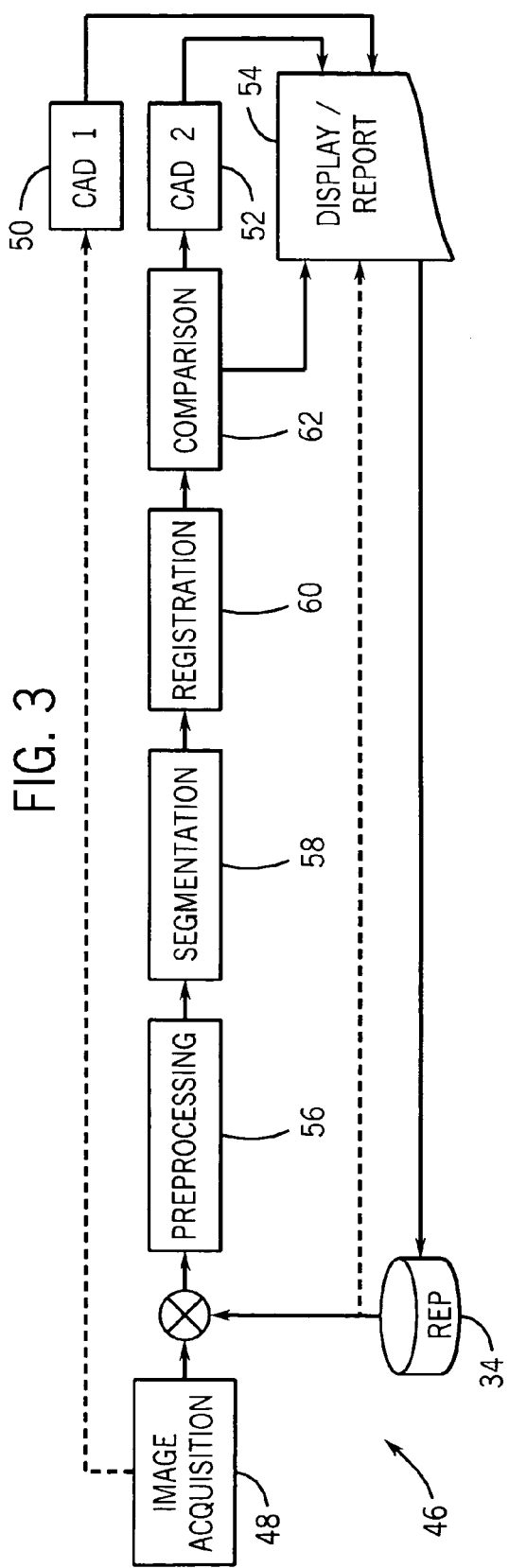
FIG. 3 is a flow diagram illustrating exemplary steps and components in implementation of the temporal analysis processing of the present technique.

System 32 will typically include an operator workstation 22 which may be the same operator workstation as that described above with reference to the imaging system 10, or a different operating station. The operating station may, itself, incorporate the image data processing circuitry 40 and may be entirely remote from the acquisition system 10. Some type of output system 44 is typically included, such as for creating hardcopy outputs images, reports, and so forth. Either operator workstation 22 or output system 44 will also include monitors for viewing reconstructed and temporal change images as discussed below, which may be presented in the form of high resolution and high contrast images permitting users and viewers to analyze, read, annotate and otherwise use the reconstructed images. System 32 implements one or more types of processing for analyzing temporal changes between images taken at different points in time. FIGS. 3, 4, 5, 6 and 7 illustrate exemplary modules and processes contemplated for system 32. In general, certain key modules may be included in the systems and workflow. FIG. 3, for example, illustrates an exemplary temporal change analysis routine 46 in accordance with the present techniques. As shown in FIG. 3, the routine begins with image acquisition as represented at block 48. Acquired image data is associated with images of similar subjects, typically the same subject and the same view, taken at earlier points in time and accessed from repository 34. The system ultimately will apply one or more CAD algorithms as represented at reference numerals 50 and 52 to produce and display or report as represented at block 54. The images acquired at different points in time are processed by a series of modules which interact with the CAD algorithms 50 and 52 as discussed below. In general, these modules include a preprocessing module 56, a segmentation module 58, a registration module 60, and a comparison module 62.

Image acquisition at block 48 of FIG. 3 enables the temporal change analysis. In general, an imaging system is provided as described above and image data is stored in a repository 34 for retrieval. Although reference is made herein to two specific images taken to different points in time that are compared by the system, it should be borne in mind that the technique can be extended to any number of images and any number of different points in time in which the images are acquired. The image data analyzed by the system can be the original unprocessed image data from the acquisition system or can be partially or fully processed versions of the original image data. Moreover, the image data may originate in the same or a different modality or imaging system. Similarly, the image data may include digitized data created by scanning and digitization of a conventional medium, such as hardcopy images and film.

Preprocessing module 56 may serve several functions, depending upon the nature of the image data. For example, module 56 may "normalize" two images to account for differences in acquisition techniques or differences in pre- and post-processing methods. As an example, in X-ray images, if the first image has half the exposure of the second image, gray levels in the first image may be multiplied by a factor of 2 before any further comparison to the second image. The adjustment in the images serves to reduce the differences in the overall image intensity due to image display or technical factors such as differences in dose. Preprocessing module 56 may also perform operations such as scaling, size and orientation adjustments, dynamic range adjustments, and so forth.

Segmentation module 58 identifies and defines the limits of features of interest in the image data at both points in time. Many types of segmentation are currently available in the art, and these processes are typically identify gradients, intensities and other characteristics of the pixilated data to extract meaningful associations of the data, such as to identify edges, areas, regions, and so forth which may represent recognizable features in the ultimate image. Module 58 therefore provides an automated or manual mechanism for isolating regions of interest in the image data. In many cases of practical interest, the entire image could be the reason of interest, with specific features or subsets of data being identified as potentially representing objects of particular interest.

Registration module 60 provides for alignment of similar regions or objects of interest in the images taken at different points in time. If the regions of interest for temporal change analysis are small, rigid body registration transformations, including translation, rotation, magnification and shearing may be sufficient to register a pair or images taken at two different points in time. However, if the regions of interest are large, including almost the entire image, warped, elastic transformations can be applied.

As will be appreciated by those skilled in the art, one manner for implementing the warped registration is the use of multi-scale, multi-region, pyramidal approach. In such approaches, a different cost function highlighting changes may be optimized at every scale. Such cost functions can be, but are not limited to, correlation methods, such as mathematical correlation and sign-change measurement, or statistical methods such as entropy measurements and mutual information. Images are re-sampled at a given scale and then divided into multiple regions. Separate shift vectors are calculated for different regions. Shift factors are interpolated to produce a smooth shift transformation, which is applied to warp one of the images. Weighting functions on shift vectors may be applied during interpolations and these weighting functions can be determined from the image characteristics, such as anatomical features, or the characteristics of the cost function map. The images are re-sampled and the warped registration process is repeated at the next higher scale until the pre-determined final scale is reached, or a point is reached where the cost function map has attained a certain pre-determined threshold. In other situations, a combination of rigid registration and elastic transformations may be used.

Following registration by the registration module 58, the images at different points in time will be comparable. The preprocessing segmentation and registration modules also serve to render the images comparable insomuch as they reduce apparent but inconsequential differences between the images that could tend to indicate more substantial changes over time than have actually occurred in the subject. Comparison module 62, then, analyzes dissimilarities between the images. A dissimilarity measure between the registered images may be performed in any one of several ways. For example, simple subtractions may be employed, wherein differences are analyzed on a pixel-by-pixel basis and an absolute value of a difference is recorded. However, enhanced methods include a division method, in which the difference between the images, on a pixel-by-pixel basis may be represented by the equation:

$$I_d = (I_1 * I_2)/(I_2 * I_2 + \Phi)$$

Where $I_1$ and $I_2$ represent image data for images taken at first and second times, respectively, and $\Phi$ represents a weighting factor. The value $I_d$ represents the value, on a pixel-by-pixel basis, of the difference, comparison or temporal change image.

Following comparison of the images, the display and report module 54 provides a display and quantification capabilities for the user to visualize or quantify the results of the temporal comparison. Results of temporal comparisons may be simultaneously displayed on a display device, such as a monitor, separate from either of the temporal images. Alternatively, either or both of the temporal images may be superimposed with one another and with the temporal change image via a logical operator based on a specified criterion. For quantitative comparison, color look-up tables for the overlaid images may be used so as to highlight differences or changes that have occurred over time. The resulting combination can be presented in a monochrome or multi-color overlay display.

In the temporal change analysis routine illustrated in FIG. 3, the workflow permits analysis of the temporal change image, and of either or both images taken at different points in time via CAD algorithms. The temporal change image is presented to the user with the possible addition of the current or previous images, as discussed above. The present technique, in addition, combines the temporal comparison processing with tools for computer aided analysis of both the original images and the temporal change image. This aspect of the present technique greatly facilitates automation, improvement and simplification of the detection process, particularly of the temporal change image. A detailed presentation of a typical CAD technique used for blocks 50 and 52 in FIG. 3 is provided below. In the routine of FIG. 3, however, features are segmented, classified and presented by CAD algorithm 50 based upon the original image. CAD algorithm 52, which may be different from CAD algorithm 50, particularly in its segmentation and classification schemes, is operated on the temporal comparison data, that is, the temporal change image. Again, one or both of these analyses may be presented by the display and report module 54. It is anticipated that improved CAD algorithms, or more generally CAX algorithms will be developed for further analysis of the temporal change image data. That is, augmentations and reductions or appearances or disappearances of features of interest at specific locations may be recognized and classified for presentation to the user in diagnosis, treatment, and so forth in the medical context, and in other contexts for analysis of quality or internal structures of subjects of interest.

Figure 4:
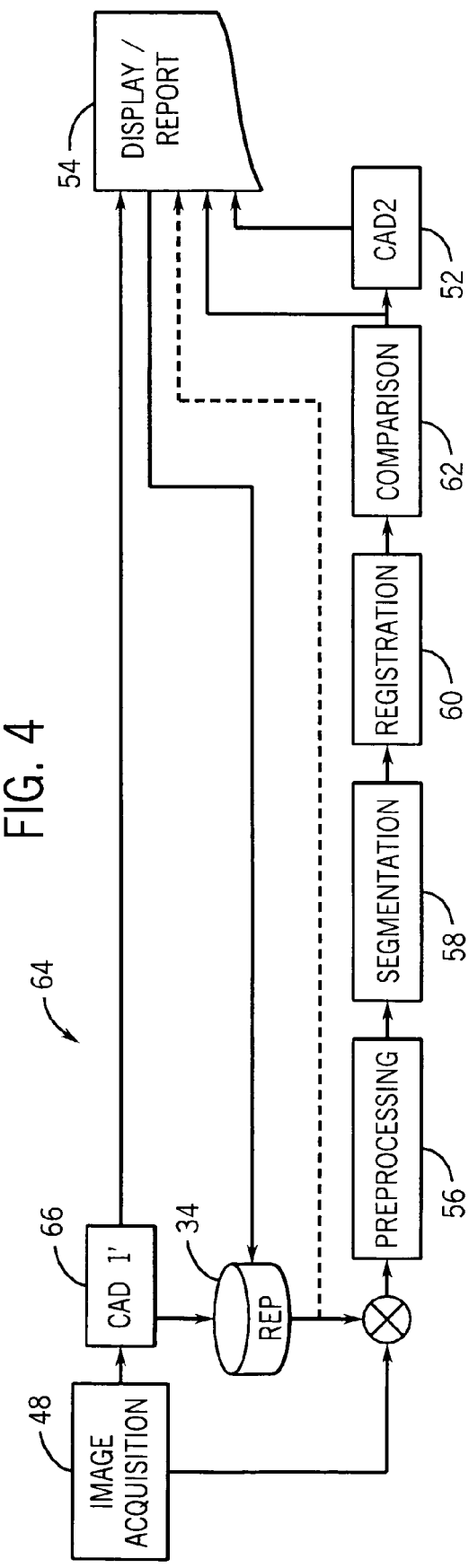
FIG. 4 is a flow diagram similar to that of FIG. 3 illustrating an alternative process for temporal analysis of images.

FIG. 4 illustrates an alternative temporal change screening routine which facilitates and enhances computational efficiency of the overall process described above. In particular, in many processes throughput an efficient image review is critical, particularly in medical contexts, parcel handling contexts, part quality control contexts, and so forth. Providing additional images for review by a human reviewer, such as the temporal change images discussed herein, may have a tendency to decrease productivity, especially in cases where no temporal change, or insignificant temporal changes have occurred. The routine of FIG. 4 addresses such workflow issues. The solution of FIG. 4 involves initiating temporal comparison only on images in which findings of potential interest are detected. That is, the routine of FIG. 4, designated generally by reference numeral 64, includes execution of a particular CAD routine process 66 prior to performing the temporal analysis. It is presently contemplated that CAD routine 66 may be different from either CAD routine 50 or 52 discussed above, and serves to initiate the temporal change analysis process. That is, the first CAD algorithm 66 used to analyze the current images may have higher sensitivity and a lower specificity than the algorithms that would normally would be applied to such image data. If the data is found to potentially represent features of particular interests, such as particular anatomies, disease states, lesions, and so forth in the medical context, or inclusions, objects of interest, defects, and so forth in other contexts, the temporal comparison steps described above are initiated. Where such features are not identified by CAD algorithm 66, a display and report module 54 may present the information resulting from the analysis, or the original images directly. Where such features are recognized, however, historical images are accessed from repository 34, and the preprocessing, segmentation, registration and comparison steps, followed by CAD algorithm 52 are performed as before. The computation of the temporal change image, and its analysis, are therefore avoided accept in cases where potentially interesting features were identified by CAD algorithm 66. The higher sensitivity and lower specificity of algorithm 66, where employed, will have a tendency to increase false positive findings which can be removed through application of the temporal comparison process, and possible application of the second CAD algorithm 52. It should be noted that the findings of both CAD algorithms 66 and 52 may be entered into a reconciliation module, described below, to summarize and simplify the data presented and reported.

Figure 5:
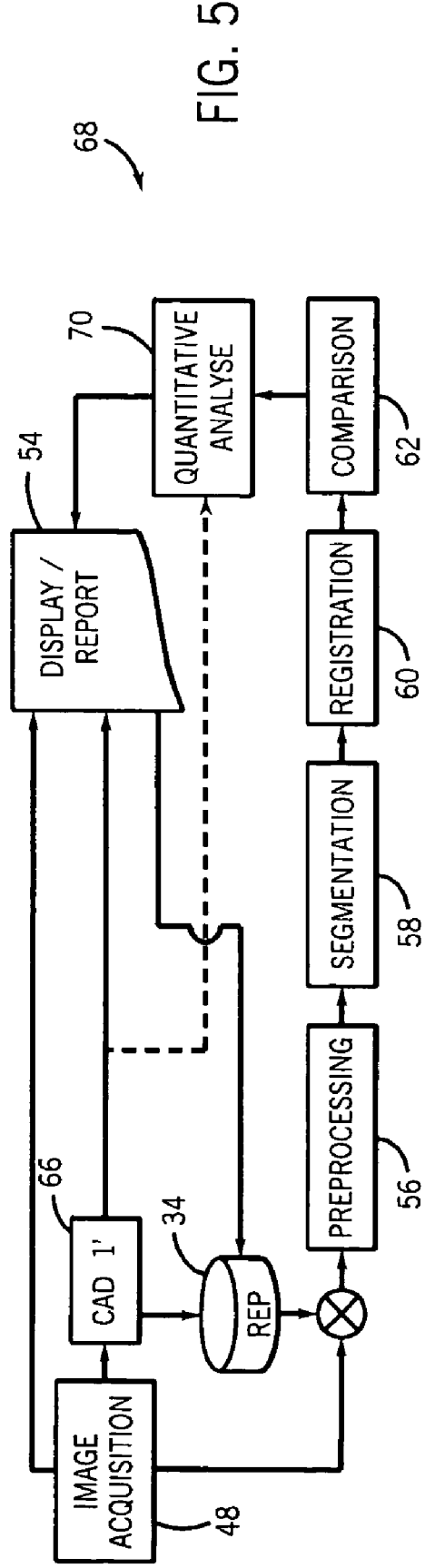
FIG. 5 is a further flow diagram illustrating another alternative process for temporal analysis of images.

The present technique also provides for quantitative analysis of temporal changes between images. FIG. 5 represents a temporal change quantitative analysis routine 68 which allows for measurement and quantification of specific changes between the images. In the workflow of FIG. 5, acquired images may be displayed directly by the display and report module 54, and are subjected to a CAD algorithm 66 for initial identification of possible features of interest. If such features are identified, previous images are accessed from repository 34, and are subjected to the preprocessing, segmentation, registration and comparison modules discussed above. Based upon the comparison, a quantitative analysis module 70 performs measurements of characteristics of the temporal change image. This information, too, can be presented in the display and report module 54. The quantitative analysis module 70 permits actual measurement of specific changes, such as by counting or accumulating a number of pixels or voxels in which significant differences between the images are present. It should be noted that, throughout the present discussion, while reference is made to comparison of pixels and two or more images, all of the present techniques may be applied to three-dimensional images and image datasets, such as to detect changes is three dimensions, rendering the process applicable to situations where the particular orientation or presentation of an object in series of images has changed over time due to actual movement or positioning of the subject in the imaging system. By use of quantitative analysis module 70, then, features such as suspicious lesions may be automatically detected in a current image, a previous image (or multiple previous images), and the same region identified, with temporal comparison calculated and analyzed for temporal changes. Thus, growth or contraction of a nodule, appearance of a pneumothorax, for example, can be quantitatively measured. Again, the quantitative information may be reported together with the temporal change image or images, the CAD images, original images, and so forth. It should be also noted that the quantitative analysis module could be used in conjunction with any of the described temporal comparison data flows mention above.

Figure 6:
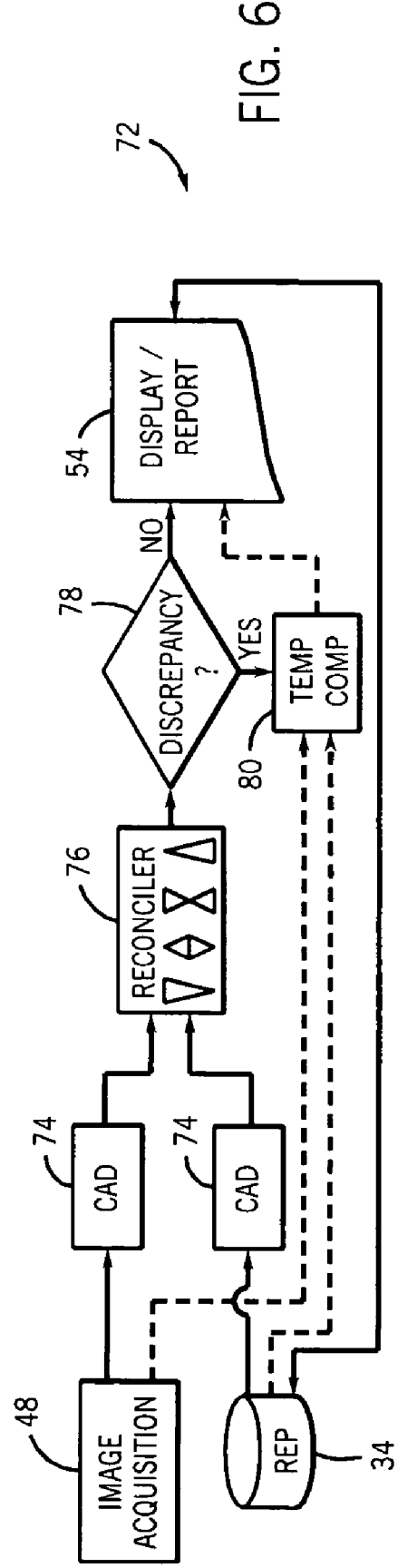
FIG. 6 is a further flow diagram illustrating exemplary steps in processing images acquired at different points in time through the use of a reconciler.

As noted above, the present technique may be employed with a reconciliation routine in which a machine or human reader identifies discrepancies between analyses. Such discrepancies may typically include concurrences and differences, such as in the recognition or classification of features of interest in temporally distinct images. FIG. 6 illustrates a temporal change reconciling routine 72 implementing such reconciliation. In the routine 72, current and previous images are accessed and a CAD algorithm 74 is performed on both. CAD algorithm 74 will segment and classify features of interest in the image data, and these results will be provided to a reconciler module 76. The reconciler module 76 will, then, recognize whether meaningful differences exist between the results of the CAD analysis. As indicated at decision block 78, if the results of the analysis of the images taken at different points in time are consistent, the image data, reconstructed images, or results of the analyses may be displayed by the display and report module 54. If, on the other hand, differences or discrepancies exist between the analyses, a temporal comparison module 80 is launched, and the preprocessing, segmentation, registration, comparison and analysis described above is performed. Temporal comparison module 80 may, furthermore, perform specific CAD algorithms, such as algorithms designed to operate on temporal change images, as well as quantitative analysis algorithms for quantifying changes represented over time, and so forth. The results of such analysis are then presented by the display and report module 54.

Figure 7:
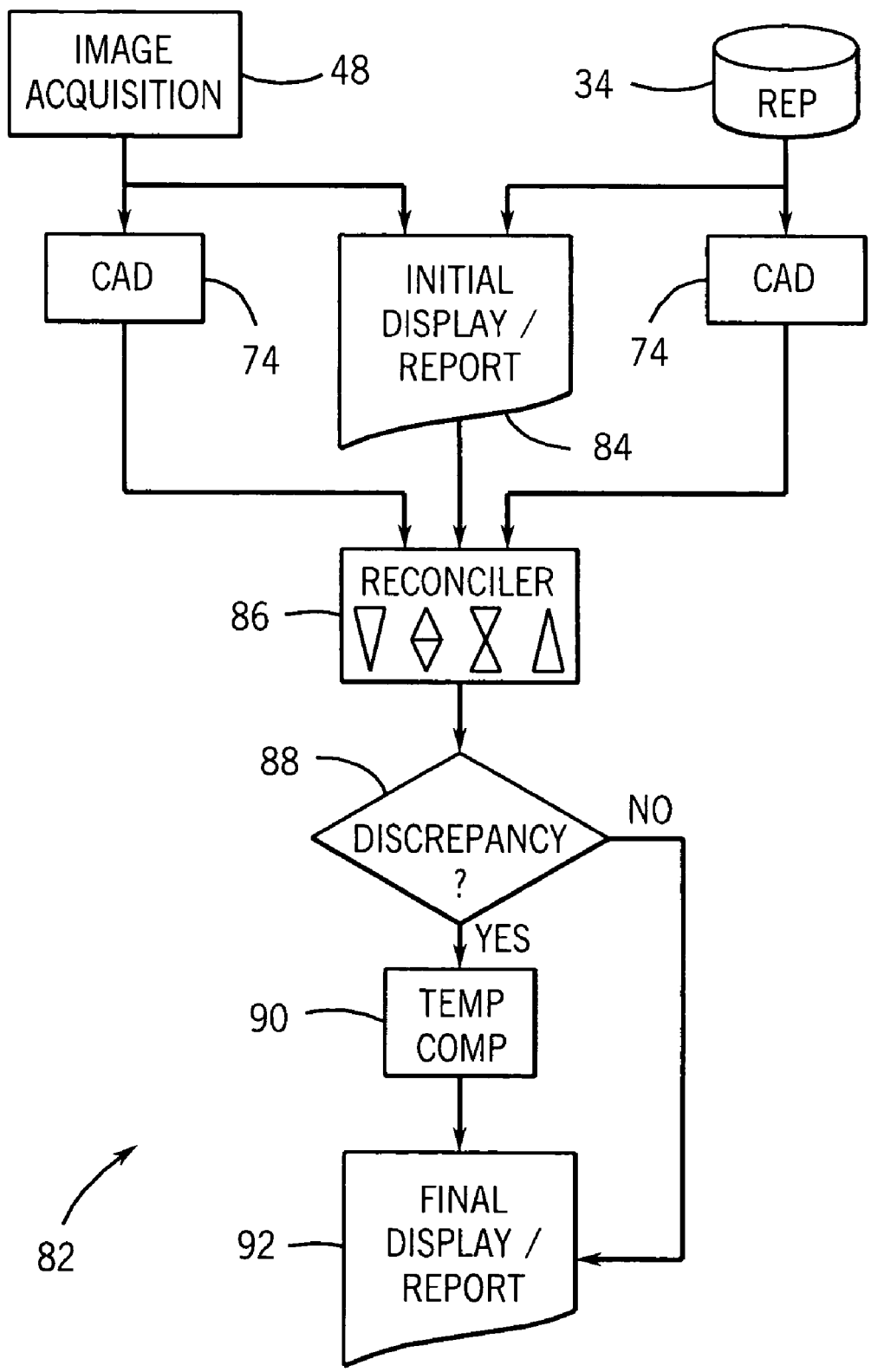
FIG. 7 is a further flow diagram illustrating another alternative process for temporal image analysis employing a reconciler.

FIG. 7 represents an alternative temporal change reconciling routine 82. In routine 82, current and previous image data is accessed and analyzed via CAD algorithms 74, as described above with reference to FIG. 6. However, an initial display and report module 84 presents both images (or multiple images from multiple points in time) to a human observer. The human observer may, then, analyze the images to identify features of potential interest for further analysis. The input from the human observer, and the results of analysis of both sets of images by CAD algorithm 74, are subjected to a reconciler 86. As with reconciler 76 described above, reconciler 86 identifies discrepancies, that is, concurrences and differences, between either the segmentation or classification performed by the CAD algorithm and by the human observer. If such discrepancies are not present, as determined by decision block 88, a final display and report module 92 produces an output for further use and storage. If, on the other hand, such discrepancies are determined between any one of the inputs to reconciler 86, the temporal comparison module 90 is initiated and preprocessing segmentation, registration, comparison, followed by CAD analysis and quantitative analysis where desired is launched.

Figure 8:
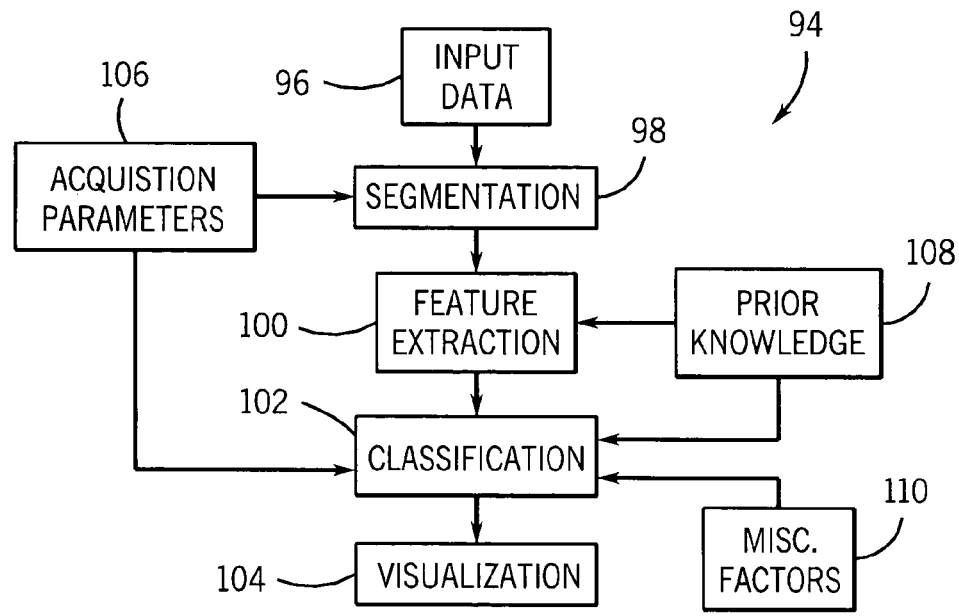
FIG. 8 is a flow diagram illustrating exemplary steps in a typical CAD routine for performing analysis of image data or temporal change images in accordance with the present technique.

In the various processes and workflows described above, various types of CAD algorithms will be implemented. As will be appreciated by those skilled in the art, such CAD processing may take many forms, depending upon the type of analysis, type of image, and type of feature of interest. FIG. 8 illustrates and exemplary illustrates an exemplary CAD routine 94 which may be adapted to such applications. By way of example, in the medical context, a medical practitioner may derive information regarding a specific disease using temporal data as described herein. A CAD algorithm with temporal analysis capabilities for analyzing changes in conditions is therefore proposed. By way of further example, in CT systems, features of interest viewable in images may be determined by temporal mammography mass analysis. Such mass identification can be performed for detection alone, such as to identify the presence or absence of suspicious candidate lesions, or may take the form of diagnosis, that is, classification of detected lesions as either benign or malignant.

In the implementation of CAD routine 94 illustrated in FIG. 8, input data 96 may be accessed either directly from a source, such as a CT data acquisition system, or from various diagnostic image datasets, such as stored in a data repository as discussed above. A segmentation module 98, then, defines regions of interest to calculate whether features are recognizable in the image data. The region of interest may be defined in several ways. For example, the entire dataset may be identified as a region of interest. Alternatively, a part of the data, such as a candidate mass region in a specific region may be considered. The segmentation of the region of interest can be performed either manually or automatically. Manual segmentation involves displaying the data and a user delineating a region via an input device, such as a mouse or other suitable interface. An automated segmentation algorithm may use prior knowledge, such as the shape, size or other image characteristics of typical similar features to automatically delineate the area of interest. A semi-automated method may employ in combination of manual and automated segmentation.

A feature extraction module 100, which may be an optional module in the routine, involves performing computations on the sourced data. For example, the image-based data in the region of interest may be analyzed to determine statistics such as shape, size, density, curvature, and so forth. On acquisition-based and patient-based data, such as that used in the medical context, the data itself may serve as the extracted features.

Once the features are segmented and any feature extraction has been performed as desired, a classification module 102 helps to classify the regions of interest in accordance with any suitable type of classification. For example, in the medical context, masses may be classified by their type, by a probability that they are benign or malignant, and so forth. Such classifiers may include a wide range of algorithms, such as Bayesian classifiers, neural networks, rule-based methods, fuzzy logic methods, and so forth. It should be noted that the CAD routine is performed once by incorporating features of all data and can be performed in parallel. The parallel operation of CAD algorithms may improve performance of the CAD operations. For example, individual operations on the datasets may be influenced by results of individual modules of the CAD algorithm or by combining the results of CAD operations, through logical operators such as AND, OR NOT operations, or combinations of these. In addition, different CAD algorithms and operations may be implemented to detect multiple features, articles, disease states, and so forth in series or in parallel, as described more fully below with reference to FIG. 9. Following the classification at module 102, some type of visualization is usually preferred as indicated at block 104 in FIG. 8. Again, the visualization may be performed via a conventional or special-purpose monitor, hardcopy printouts, film, or any other suitable manner.

It should be noted that the CAD routine may make use of specific information relating to the images, or general information relating to knowledge with respect to particular features of interest anticipated in the images for the feature extraction and classification steps, as well as for segmentation. As illustrated in FIG. 8, acquisition parameters 106 are generally relevant to the manner in which features of interest will be presented and can be identified from the images. Such acquisition parameters may typically include the type of system generating the image protocols and settings used to generate the image data, and so forth. Moreover, various types of prior knowledge will be useful in the CAD process as indicated at block 108. Such prior knowledge may typically include statistical analyses of similar features or objects which may be identified in the images for analysis. Many types of characteristics may be identified by analysis of the image data, and the prior knowledge of similar characteristics exhibited by confirmed features of the same type is extremely useful in the feature extraction and classification modules, although this information may also be used in segmentation. Finally, other factors may be taken into account in the process, particularly for classification, as indicated at block 110 in FIG. 8. Such factors may include demographic factors, risk factors, and so forth which may aid in the final classification of any recognized features in the image data.

In a preferred process, some type of training of the CAD algorithm is provided, such as through the incorporation of prior knowledge of known and confirmed features of interest. Training phases of this type may involve computation of several candidate features based on known samples, such as benign and malignant masse in the medical context. A feature selection algorithm is then employed to sort the candidate features and select only the useful features for confirming or rejecting certain segmentation, feature extraction and classification candidates. Only useful features or characteristics are preferably retained to reduce redundancy and to improve computational efficiency. Such decisions are typically based on classification of results with different combinations of candidate features. The feature selection algorithm employed is also used to reduce the dimensionality from a practical standpoint, therefore further improving computational efficiency. A feature set is thus derived that can optimally discriminate between features of interest, such as benign and malignant masses in the medical context. This optimal feature set is extracted on regions of interest in the CAD routine. Optimal feature selection can be performed using many techniques, such as well-known distance measure techniques, including diversions measures, Bhattacharya distance measures, Mahalanobis distance measures, and so forth.

The CAD algorithms employed in the present technique may be different from one another, and indeed multiple different CAD algorithms may be used. For example, as described above, algorithms may be used for parallel analysis of image data, or may be used in series, such as to launch temporal analysis only where particular features of interest may be present or viewable in the image data. Parallel CAD algorithms may also be employed for the same or different features, or with different levels of sensitivity and specificity, with reconcilers being employed as discussed above, where appropriate. Moreover, as noted above, it is anticipated that temporal analysis CAD algorithms will continue to be developed for operation on temporal change images specifically. These will include algorithms for quantitative analysis of changes over time.

Figure 9:
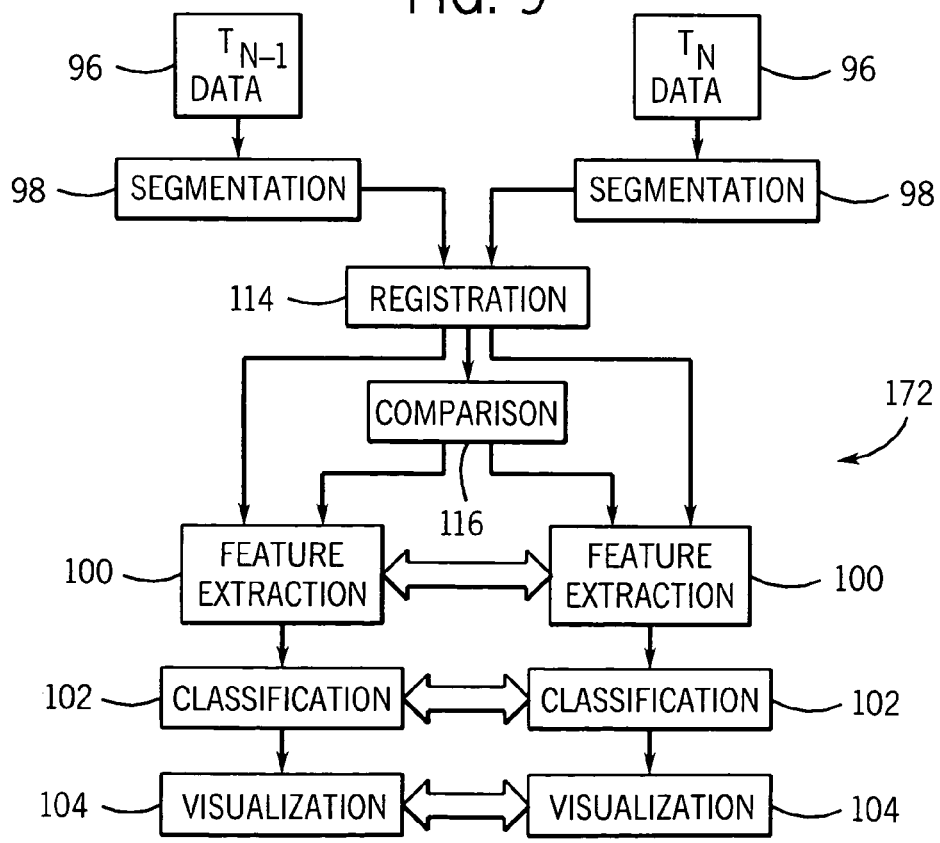
FIG. 9 is a flow chart representing an alternative process for analyzing images created at different points in time interactively in accordance with aspects of the present technique.

As also mentioned above, certain CAD algorithms may be performed or implemented in parallel as represented generally in FIG. 9. The interactive temporal analysis CAD routine, designated generally by reference numeral 112 in FIG. 9, allows for temporal changes between images to be analyzed through interactive or interleaved operation of CAD modules of the type discussed above. By way of example, image datasets 96 are accessed from different points in time, and segmentation is performed on each by a segmentation module 98 of two parallel CAD algorithms. In general, the CAD algorithms may be of the same nature, or may differ from one another, such as in sensitivity or specificity, or may be adapted to identify different features of interest. At step 114 the segmented images, or segmented portions of the images are registered by a specially-adapted registration module. The operation of registration module 114 may be generally similar to that of registration module 60 discussed above, or may be specially adapted for different types of images or segmentation where the segmentation performed by the CAD algorithms of the routine are different. The results of the registration are provided to a comparison module 116 which determines whether the results of the segmentation are convergent or divergent. The output of the registration may also be provided to feature extraction modules 100. From this point on, data between the modules of each CAD algorithm may be exchanged or used in a complimentary fashion to enhance feature extraction, classification and eventual visualization. Certain results of the CAD algorithms are thus merged prior to the feature identification. The resulting process allows for temporal differences between images to be identified, taking into account feature commonalities and differences, to arrive at a synergistic analysis of the temporal data represented by the different image datasets.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for analyzing image data comprising:
generating a temporal change image based upon first and second images from different times by segmenting the first and second images and registering at least a portion of the segmented images with one another, wherein the first and second images are generated by different imaging modalities; and analyzing the temporal change image via at least one CAD algorithm.

2. The method of claim 1, wherein analyzing the temporal change image via the CAD algorithm includes diagnosing a physical condition of a patient.

3. The method of claim 1, wherein the CAD algorithm identifies at least one feature of interest in the temporal change image.

4. The method of claim 1, comprising performing quantitative analysis on the temporal change image.

5. The method of claim 4, wherein the quantitative analysis includes determining a change in size of a feature of interest between the first and second images based upon the temporal change image.

6. The method of claim 1, comprising presenting a report to a user along with at least one of the first image, the second image and the temporal change image.

7. The method of claim 1, comprising analyzing at least the first image via a second CAD algorithm.

8. A method for analyzing image data comprising:
analyzing a first image via at least one CAD algorithm to identify a feature of interest;
if a feature of interest is identified in the first image, accessing a second image from a different time than the first image and generating a temporal change image based upon the first and second images; and analyzing the temporal change image via a second CAD algorithm different from the CAD algorithm used for analyzing the first image: wherein the CAD algorithm used for analyzing the first image has a sensitivity and a specificity to produce a desired level of positive identifications of potential features of interest, and wherein the CAD algorithm used for analyzing the temporal change image is configured to reduce the positive identifications of features of interest.

9. The method of claim 8, comprising reporting results of the analysis to a user if a feature of interest is not identified in the first image.

10. The method of claim 8, wherein the temporal change image is generated by segmenting the first and second images and registering the segmented images with one another.

11. The method of claim 8, comprising performing quantitative analysis on the temporal change image.

12. The method of claim 11, wherein the quantitative analysis includes determining a change in size of a feature of interest between the first and second images based upon the temporal change image.

13. The method of claim 8, comprising presenting a report to a user along with at least one of the first image, the second image and the temporal change image.

14. A method for analyzing image data comprising:
analyzing a first image via at least one CAD algorithm to identify a feature of interest; and
if a feature of interest is identified in the first image, accessing a second image from a different time than the first image and analyzing the first and second images; wherein analyzing the first and second images includes Quantifying a change in a feature of interest between the first image and the second image.

15. A system for analyzing image data comprising:
means for generating a temporal change image based upon first and second images from different times by segmenting the first and second images and registering at least a portion of the segmented images with one another, wherein the first and second images are generated by different imaging modalities; and
means for analyzing the temporal change image via at least one CAD algorithm.

16. A system for analyzing image data comprising:
means for analyzing a first image via at least one CAD algorithm to identify a feature of interest;
means for accessing a second image from a different time than the first image if a feature of interest is identified in the first image, and for generating a temporal change image based upon the first and second images; and
means for analyzing the temporal change image via a second CAD algorithm different from the CAD algorithm used for analyzing the first image: wherein the CAD algorithm used for analyzing the first image has a sensitivity and a specificity to produce a desired level of positive identifications of potential features of interest, and wherein the CAD algorithm used for analyzing the temporal change image is configured to reduce the positive identifications of features of interest.

17. A system for analyzing image data comprising:
means for analyzing a first image via at least one CAD algorithm to identify a feature of interest; and
means for accessing a second image from a different time than the first image if a feature of interest is identified in the first image, and for analyzing the first and second images; wherein analyzing the first and second images includes quantifying a change in a feature of interest between the first image and the second image.

18. A computer-readable medium embodied with a computer program for analyzing image data comprising:
code stored on the computer-readable medium for generating a temporal change image based upon first and second images from different times by segmenting the first and second images and registering at least a portion of the segmented images with one another, and analyzing the temporal change image via at least one CAD algorithm, wherein the first and second images are generated by different imaging modalities.

19. A computer-readable medium embodied with a computer program for analyzing image data comprising:
code stored on the computer-readable medium for analyzing a first image via at least one CAD algorithm to identify a feature of interest, and if a feature of interest is identified in the first image, accessing a second image from a different time than the first image and generating a temporal change image based upon the first and second images, and for analyzing the temporal change image via a second CAD algorithm different from the CAD algorithm used for analyzing the first image; wherein the CAD algorithm used for analyzing the first image has a sensitivity and a specificity to produce a desired level of positive identifications of potential features of interest, and wherein the CAD algorithm used for analyzing the temporal change image is configured to reduce the positive identifications of features of interest.

20. A computer-readable medium embodied with a computer program for analyzing image data comprising:
code stored on the computer-readable medium for analyzing a first image via at least one CAD algorithm to identify a feature of interest, and if a feature of interest is identified in the first image, accessing a second image from a different time than the first image and analyzing the first and second images, wherein analyzing the first and second images includes quantifying a change in a feature of interest between the first image and the second image.

* * * * *